US009551667B2

(12) United States Patent
Schmidt et al.

(10) Patent No.: US 9,551,667 B2
(45) Date of Patent: Jan. 24, 2017

(54) METHOD FOR AMPLIFICATION-FREE NUCLEIC ACID DETECTION ON OPTOFLUIDIC CHIPS

(75) Inventors: Holger Schmidt, Capitola, CA (US); Aaron Roe Hawkins, Provo, UT (US)

(73) Assignees: The Regents of the University of California, Oakland, CA (US); Brigham Young University, Provo, UT (US)

( * ) Notice: Subject to any disclaimer, the term of this patent is extended or adjusted under 35 U.S.C. 154(b) by 140 days.

(21) Appl. No.: 13/988,217

(22) PCT Filed: Nov. 18, 2011

(86) PCT No.: PCT/US2011/061484
§ 371 (c)(1),
(2), (4) Date: May 17, 2013

(87) PCT Pub. No.: WO2012/068511
PCT Pub. Date: May 24, 2012

(65) Prior Publication Data
US 2013/0244227 A1    Sep. 19, 2013

Related U.S. Application Data

(60) Provisional application No. 61/415,482, filed on Nov. 19, 2010.

(51) Int. Cl.
*C12Q 1/68*    (2006.01)
*C12P 19/34*    (2006.01)
(Continued)

(52) U.S. Cl.
CPC ..... *G01N 21/6486* (2013.01); *B01L 3/502715* (2013.01); *C12Q 1/6818* (2013.01);
(Continued)

(58) Field of Classification Search
USPC ... 435/6.1, 6.11, 91.1, 287.1, 287.2; 436/94, 436/501; 536/23.1, 24.3, 24.33; 977/704, 977/724, 728, 756, 773, 797, 799, 800, 977/802, 803, 804
See application file for complete search history.

(56) References Cited

U.S. PATENT DOCUMENTS

2002/0034747 A1* 3/2002 Bruchez et al. .................. 435/6
2004/0043954 A1* 3/2004 Gregoriadis .................... 514/44
(Continued)

FOREIGN PATENT DOCUMENTS

WO    WO 2010/045357 A2    4/2010
WO    WO 2012/068511 A2    5/2012

OTHER PUBLICATIONS

"Optofluidics" from Wikipedia, the free encyclopedia. Printed on Mar. 6, 2015.*
(Continued)

*Primary Examiner* — Frank Lu
(74) *Attorney, Agent, or Firm* — Baker & Hostetler LLP

(57) ABSTRACT

An optofluidic platform is constructed so as to comprise a planar, liquid-core integrated optical waveguides for specific detection of nucleic acids. Most preferably, the optical waveguides comprises antiresonant reflecting optical waveguide (ARROWs). A liquid solution can be prepared and introduced into the optofluidic platform for optical excitation. The resulting optical signal can be collected at the edges of the optofluidic platform and can be analyzed to determine the existence of a single and/or a specific nucleic acid.

17 Claims, 4 Drawing Sheets

(51) Int. Cl.
    *C12M 1/34*     (2006.01)
    *C12M 3/00*     (2006.01)
    *C07H 21/02*     (2006.01)
    *C07H 21/04*     (2006.01)
    *G01N 21/64*     (2006.01)
    *G01N 21/03*     (2006.01)
    *B01L 3/00*     (2006.01)

(52) U.S. Cl.
    CPC ........... *C12Q 1/6825* (2013.01); *G01N 21/03* (2013.01); *G01N 21/6428* (2013.01); *B01L 2200/0647* (2013.01); *B01L 2200/12* (2013.01); *B01L 2300/0816* (2013.01); *B01L 2300/0819* (2013.01); *B01L 2300/0887* (2013.01); *B01L 2400/0415* (2013.01); *G01N 2021/0346* (2013.01)

(56) References Cited

U.S. PATENT DOCUMENTS

2006/0194206 A1\*   8/2006   Persson et al. ................... 435/6
2006/0251371 A1   11/2006   Schmidt et al.

OTHER PUBLICATIONS

Chen, A. et al., "Planar FRET detection from biomolecules on an optofuluidic chip", Proc Spie 7606, Silicon Photonics V, vol. 7606, Feb. 16, 2010 pp. 1-7.
Measor P, et al., "Tailorable integrated optofluidic filters for biomolecular detection", Lab Chip. Mar. 7, 2011;11(5):899-904.
Tyagi S, et al., "Molecular beacons: probes that fluoresce upon hybridization", Nat Biotechnol. Mar. 1996;14(3):303-8.
Kim S, et al., "Rapid DNA hybridization analysis using a PDMS microfluidic sensor and a molecular beacon", Anal Sci. Apr. 2007;23(4):401-5.
International Patent Application No. PCT/US2011/061484: International Search Report and Written Opinion dated Jul. 19, 2012, 9 pages.
Yin et al, "Planar optofluidic chip for single particle detection, manipulation, and analysis", Lab on a chip, Jun. 27, 2007, 7(9), 1171-1175.
Yin et al, "Single-molecule detection sensitivity using planar integrated optics on a chip" Optics Letters, Jul. 15, 2006, 31(14), 2136-2138.
European Patent Application No. 11842361.5; Office Action Article 94(3); Dated May 13, 2016; 6 pages.

\* cited by examiner

METHOD FOR AMPLIFICATION-FREE NUCLEIC ACID DETECTION ON OPTOFLUIDIC CHIPS

CROSS-REFERENCE TO RELATED APPLICATIONS

This application is the National Stage of International Application No. PCT/US2011/061484, filed Nov. 18, 2011, which claims the benefit of U.S. Provisional Application No. 61/415,482, filed Nov. 19, 2010, the disclosures of which are incorporated herein by reference in their entireties.

GOVERNMENT SUPPORT

This invention was made with government support under Grant No. R01-EB006097 awarded by the National Institutes of Health/National Institute of Biomedical Imaging and Bioengineering. The government has certain rights in the invention.

TECHNICAL FIELD

The present invention relates generally to the field of integrated optics, and more particularly to an optofluidic platform for optical particle detection without the need for advanced microscopy equipment. The optofluidic platform can comprise planar, liquid-core integrated optical waveguides for specific detection of nucleic acids. The optical waveguides can employ antiresonant reflecting optical waveguides, known as ARROWs or ARROW waveguides.

BACKGROUND

Nucleic acid testing (NAT) is an essential part of the rapidly growing field of molecular diagnostics (MDx). It allows for patient specific diagnostics on the genome level as well as for perfect identification of pathogens, e.g. discrimination between different virus strains.

The current gold standard for nucleic acid testing of viruses and other organisms is real-time polymerase chain reaction (RT-PCR) followed by sequencing. RT-PCR requires highly skilled operators, expensive reagents and tightly controlled reaction environments. This is largely due to the need for amplification of viral nucleic acids to generate large enough signals for readout. These limitations suggest a critical need for a new type of diagnostic instrument for amplification-free viral detection that is rapid, sensitive, reliable, and quantitative.

SUMMARY

We introduce a different approach to nucleic acid testing based on planar optofluidics—the combination of both integrated optical and fluidic components in the same miniaturized system. This approach uses planar, liquid-core integrated optical waveguides for specific detection of nucleic acids. This novel strategy enables the construction of compact, planar devices with sufficient sensitivity to detect fluorescently labeled nucleic acids from small (microliters) sample volumes without the need for costly and time-consuming target amplification. The simultaneous emphasis on vertical functional integration of optical and fluidic capabilities permits interfacing the detection element with standard fiber optics and microfluidics. The combination of these innovative aspects eliminates the key obstacles to versatile point-of-care viral analysis for a multitude of applications in clinical settings, biomedicine, analytical chemistry and other fields.

In a presently preferred embodiment of the invention, an optofluidic chip is constructed so as to comprise a self-contained, planar optofluidic platform for optical particle detection. In a further embodiment, the optofluidic platform can comprise hollow-core antiresonant reflecting optical waveguides (ARROWs), solid-core ARROWs, and fluidic reservoirs. The configuration of the different components of the optofluidic platform can allow liquids to be introduced into the hollow-core ARROWs and sub-picoliter volumes thereof to be optically excited for single particle detection.

In an embodiment, a liquid solution can be introduced into the optofluidic platform and can be optically excited to generate signal. The generated signal can be collected using, for example, a photodiode and can be analyzed. The analysis can comprise determining the existence of a fluorescence signal generated by a fluorophore attached to a nucleic acid, which can indicate the existence of a single nucleic acid particle contained in the liquid solution. As an example of a fluorophore, a molecular beacon specific to a particular nucleic acid can be prepared and introduced into the optofluidic platform. As such, the generated signal can indicate the existence of the specific nucleic acid. In an embodiment, the collected signal can be further analyzed using techniques such as a fluorescence correlation spectroscopy.

Other aspects of illustrative embodiments of the invention are described below.

DETAILED DESCRIPTION OF ILLUSTRATIVE EMBODIMENTS

Optofluidics is a rapidly growing field that deals with the interplay of optics and fluids, typically liquids, at the microscale. Currently, the major research trends include optical devices defined by fluids, optical particle manipulation in liquids, and optical particle detection and analysis, especially in biology and biomedicine.

We have invented an optofluidic approach to amplification-free nucleic acid testing that is based on liquid-core optical waveguides that maximizes the interaction between light and sample analytes. Based on creating hollow-core antiresonant reflecting optical waveguides (ARROWs), we have developed a self-contained, planar optofluidic platform for optical particle detection with extremely high sensitivity but without the need for advanced microscopy equipment. The basic layout of this platform along with the fabrication steps for forming the hollow-core waveguides are shown in FIG. 1.

Figure 1:
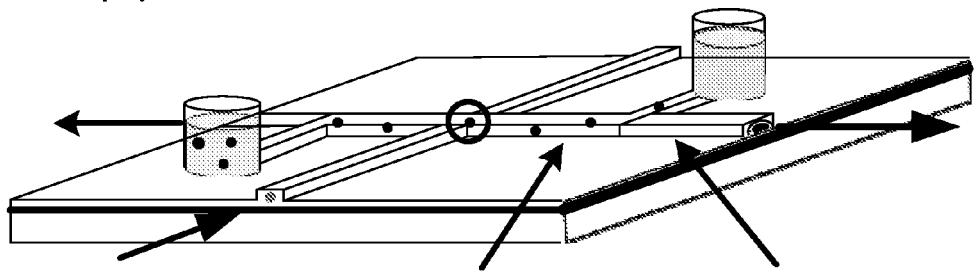
FIG. 1: Planar optofluidic platform. (a) schematic layout, images of waveguide cross sections and completed chip; (b) key microfabrication process steps for creating liquid-core waveguides.
Figure 1:
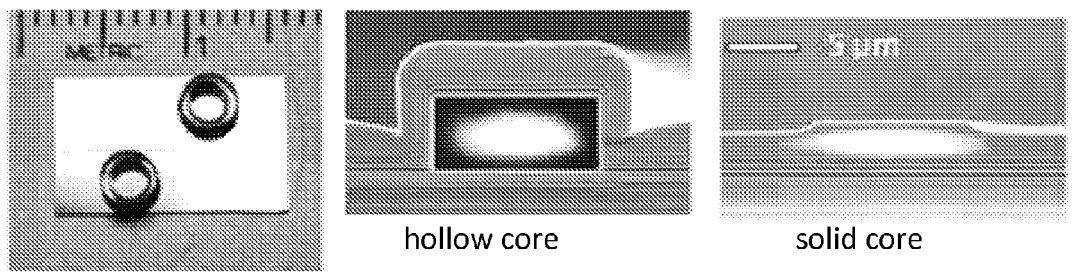
Figure 1:
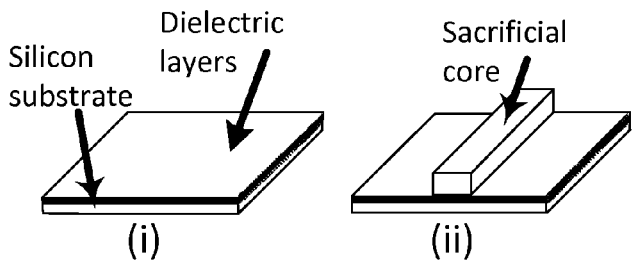
Figure 1:
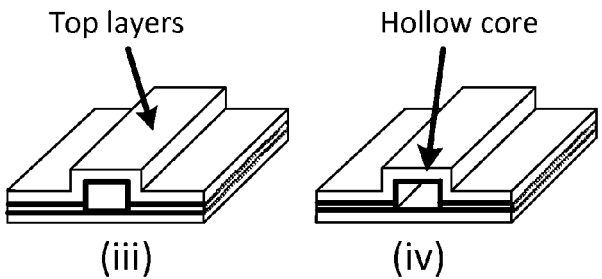

The scanning electron image in the bottom center of FIG. 1 shows a cross section of such a waveguide with hollow-core dimensions of 5×12 µm. In addition, solid-core ARROW waveguides (see SEM in bottom right of FIG. 1a) are connected to different points of the liquid core. This creates separate access paths for liquids and light into the main channel, and can also be used to define optical excitation areas with sub-picoliter volumes to achieve single molecule sensitivity. FIG. 1a depicts a typical experimental layout in which excitation light (green; arrow pointing into the optofluidic platform) enters the liquid core through an orthogonally intersecting solid-core ARROW. Generated light (red; arrow pointing out from the optofluidic platform) is collected perpendicularly in the chip plane and guided to the chip edges for detection. Fluidic reservoirs at the channel ends allow for easy channel filling and insertion of electrodes to induce electrokinetic particle movement. The photograph in the bottom left of FIG. 1a illustrates the compact size of a completed optofluidic chip.

The fabrication process shown in FIG. 1b includes (i) deposition of dielectric layers (e.g. SiO2 and SiN) of the correct thickness on a silicon substrate; (ii) patterning of a sacrificial material (e.g. SU-8) into the desired hollow-core shape; (iii) covering the sacrificial layer with additional ARROW guiding layers; and (iv) removal of the sacrificial core with chemical etching after exposing its ends by plasma etching. It can be used flexibly to define a variety of optical and fluidic layouts with microscale precision.

The platform depicted in FIG. 1 has successfully been used for detection and analysis of a variety of molecules, including fluorescence detection of single dye molecules, fluorescence correlation analysis of liposomes and ribosomes, and surface-enhanced Raman detection of rhodamine 6G molecules.

This invention disclosure introduces the use of the optofluidic platform for amplification-free molecular diagnostics of viruses.

Such a method requires both a suitable optical readout mechanism and sufficient detection sensitivity.

Optical Virus Detection

Figure 2:
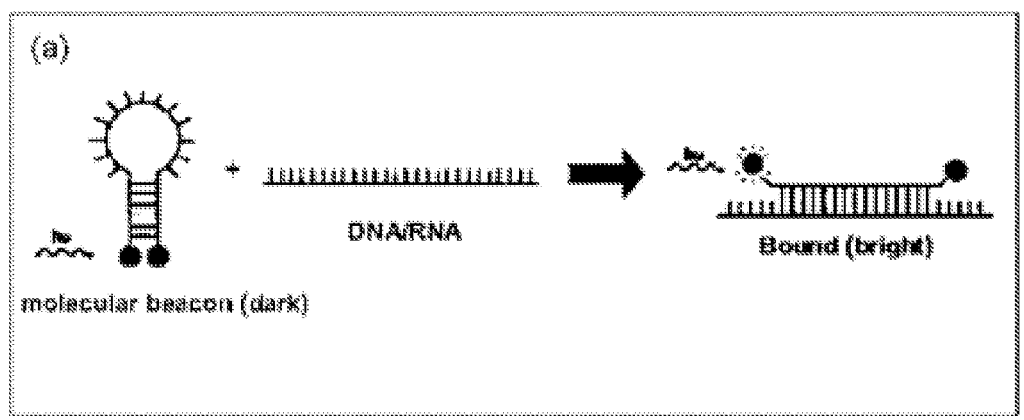
FIG. 2: Concepts of (a) molecular beacon, (b) fluorescence resonance energy transfer (FRET).
Figure 2:
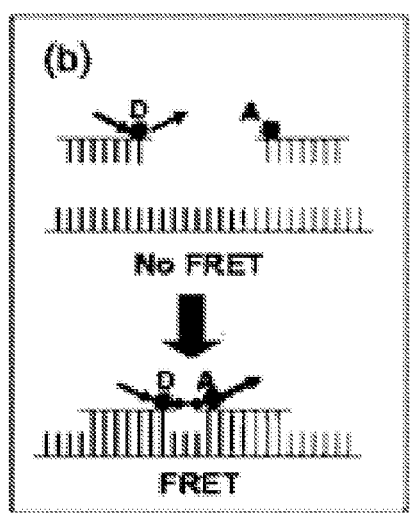

Optical detection methods play a large role in viral detection. Among these, fluorescence-based techniques are dominant. Typically, dye molecules or semiconductor quantum dots that efficiently re-emit light at a longer wavelength after optical excitation are attached to the target substance. Two advanced fluorescence methods used for virus detection, and of relevance to this application, are molecular beacon and FRET detection. FIG. 2a illustrates the principle of a molecular beacon, a short sequence of oligonucleotides that is furnished with a fluorescent dye and a quencher molecule at its ends. In the "off" state, the beacon forms a hairpin bringing fluorophore and quencher into close proximity and preventing fluorescence. When binding to a matching sequence on a DNA or RNA target, the beacon opens and hybridizes which results in fluorescence emission from the now unquenched dye. Beacons have the advantage of low background signal (no fluorescence signal in hairpin conformation) and high sensitivity for single base-pair mismatches. A drawback is the potential to unfold, especially in the presence of enzymes and proteins. Beacons are commercially available once suitable nucleotide sequences are provided.

The principle of fluorescence resonance energy transfer (FRET) applied to the identification of genetic material is shown in FIG. 2b. Two dye molecules (donor D, acceptor A) are attached to short nucleotide sequences. Nonradiative energy transfer between donor and acceptor can lead to acceptor fluorescence even if only the donor is excited. The efficiency of this energy transfer depends strongly on the proximity of the two dyes, and a measurable acceptor signal is only observed when both probes are bound to a target with matching sequence (bottom).

Both molecular beacons and FRET detection create a detectable fluorescence signal with high specificity. In addition, both techniques have successfully been used for single molecule analysis and for fluorescence-based virus detection.

Molecular beacons and FRET are two examples for how nucleic acid specific optical signals can be created for detection on the optofluidic chip.

High-Sensitivity Detection on Integrated Chip

Figure 3:
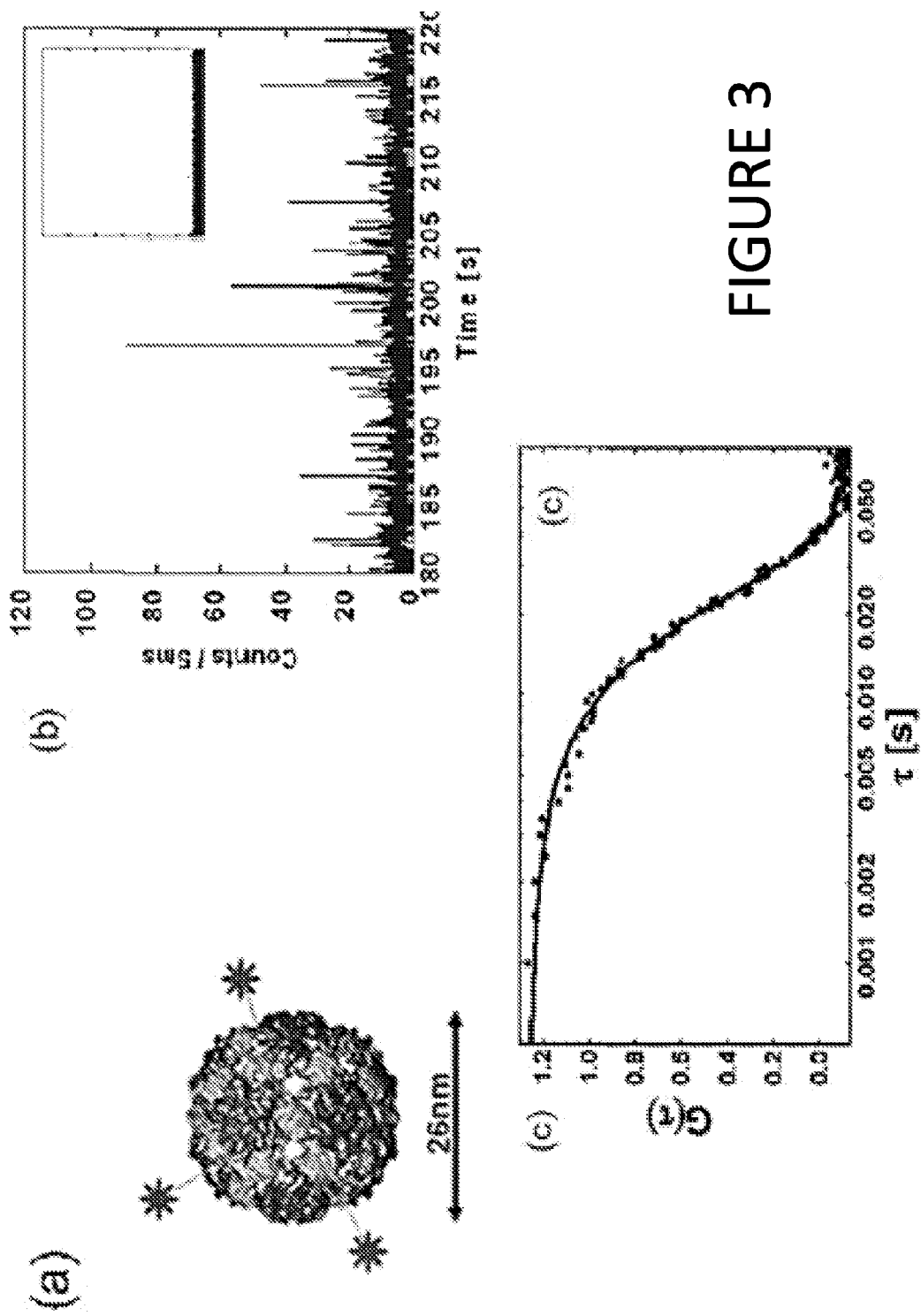
FIG. 3: On-chip virus detection. (a) Q-β phage capsid labeled with Alexa dye; (b) fluorescence signal recorded with virus in ARROW channel. Bursts indicate single particle detection events (inset: buffer baseline); (c) corresponding autocorrelation $G(\tau)$ of fluorescence fluctuations showing sub-single particle sensitivity ($G(0)>1$) and excellent agreement with theory (red line; solid line).

The second key requirement for amplification-free detection is the ability to detect fluorescence of biological samples at the single particle level. Of particular interest in this context is our recent demonstration of ultrasensitive virus detection. Fluorescently labeled Q-E bacteriophage viruses (FIG. 3a) in solution were introduced into our optofluidic chip through fluid reservoirs at one end of the hollow-core channel and optically excited at the intersection between liquid- and solid-core waveguides. The generated signal was collected along the liquid-core waveguide (see FIG. 1) and results in clear fluorescence bursts due to single virus particles (FIG. 3b) that are not present if pure buffer solution is tested (inset to FIG. 3b). The single particle sensitivity is confirmed by the fluorescence correlation spectrum (FIG. 3c) where a signal above one indicates less than a single particle in the excitation volume. The correlation signal also allowed us to extract the diffusion coefficient of the detected particles which showed good agreement with the reported value for Q-β, further corroborating the successful detection of viral particles.

To date, this is the only demonstration of single virus detection on a chip without the use of a microscope, and establishes planar optofluidic detection as a suitable method for highly sensitive bioparticle detection. However, a second necessary step is to demonstrate specific detection of a virus type and strain. To this end, we designed a molecular beacon specific for the L1 gene of human papillomavirus HPV-18. The relevant region within the HPV genome and the 30 mer beacon structure are shown in FIGS. 4a and 4b, respectively. Molecular beacons were mixed with matching oligonucleotides of various concentration. Beacon binding was facilitated by brief heating (95° C.) followed by a cool down period (50° C. for 3 min). Beacon fluorescence was then excited with 2 mW of laser light at 633 nm and detected as shown in FIG. 1a. The resulting signal is depicted in FIG. 4c and shows clear beacon fluorescence followed by photobleaching when compared to the target-free negative background (inset), even at the lowest concentration of 10 pM. FIG. 4d displays the signal dependence on target concentration and corresponding average number of molecules in the excitation volume. It shows both a linear behavior and demonstrates unequivocally our capability to detect viral DNA using molecular beacon fluorescence on the planar optofluidic ARROW platform with single molecule sensitivity.

Figure 4:
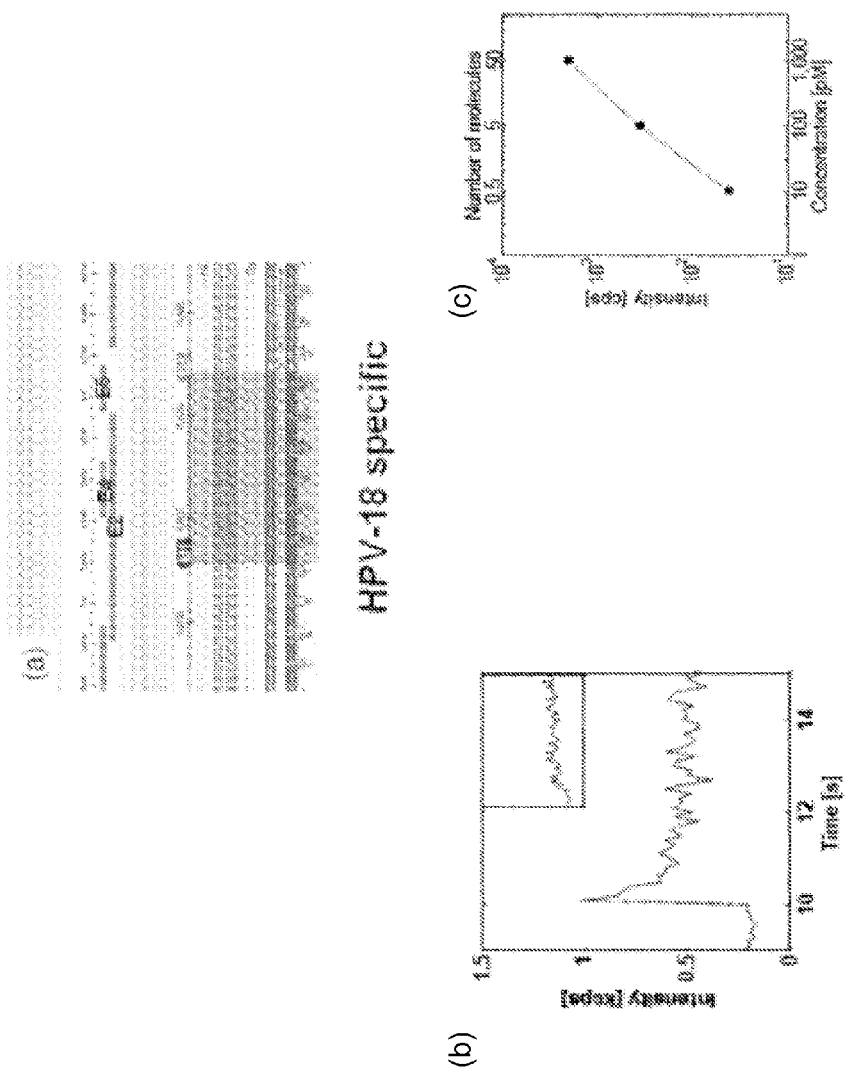
FIG. 4: On-chip amplification-free virus detection. (a) strain-specific segment of HPV-18 genome; (b) fluorescence signal (red; solid line) for on-chip beacon detection at 10 pM target concentration (inset: background); (c) fluorescence signal versus target concentration/number of molecules in excitation volume.

We note that while these results clearly show the ability to detect nucleic acids specifically in an optofluidic device, the data of FIG. 4 were measured in a "static" configuration where the channel contents were not moving. The preferred implementation for the amplification-free nucleic acid detector would be to detect nucleic acids within a moving stream of analyte liquid that is moving past the excitation point.

To date, this is the only demonstration of single virus detection on a chip without the use of a microscope, and establishes planar optofluidic detection as a suitable method for highly sensitive bioparticle detection. However, a second necessary step is to demonstrate specific detection of a virus type and strain. To this end, we designed a molecular beacon specific for the L1 gene of human papillomavirus HPV-18. The relevant region within the HPV genome is shown in FIG. 4a. By way of example and without limitation, hairpin beacon structure with fluorescent label (F, TYE665) and quencher (Q, Iowa Black), on 5' and 3' ends, respectively. Molecular beacons were mixed with matching oligonucleotides of various concentration. Beacon binding was facilitated by brief heating (95° C.) followed by a cool down period (50° C. for 3 min). Beacon fluorescence was then excited with 2 mW of laser light at 633 nm and detected as shown in FIG. 1a. The resulting signal is depicted in FIG. 4b and shows clear beacon fluorescence followed by photo-bleaching when compared to the target-free negative background (inset), even at the lowest concentration of 1 OpM. FIG. 4c displays the signal dependence on target concentration and corresponding average number of molecules in the excitation volume. It shows both a linear behavior and demonstrates unequivocally our capability to detect viral DNA using molecular beacon fluorescence on the planar optofluidic ARROW platform with single molecule sensitivity.

What is claimed:

1. A method for amplification-free detection of the presence of a specific nucleic acid sequence in a sample, comprising:
    introducing a liquid solution into one of hollow-core antiresonant reflecting waveguides (ARROWs) of a planar optofluidic platform, the liquid solution comprising said specific nucleic acid sequence and a nucleic acid probe labeled with fluorophores, wherein said nucleic acid probe specifically hybridizes with said specific nucleic acid sequence in the liquid solution;
    inducing electrokinetic particle movement to the liquid solution in the one of the hollow-core ARROWs;
    optically exciting the fluorophores using the planar optofluidic platform, thereby producing a fluorescent signal, wherein said optically exciting the fluorophores comprises injecting light into one of solid-core ARROWs of the planar optofluidic platform such that the light injected into the one of the solid-core ARROWs of the planar optofluidic platform is guided to an optical excitation region having a sub-picoliter volume at an intersection of the one of the hollow-core ARROWs and the one of the solid-core ARROWs;
    collecting the fluorescent signal using a photodetector and converting the fluorescent signal to an electrical current or a voltage; and
    detecting the presence of the specific nucleic acid sequence by analyzing the electrical current or the voltage such that the presence of the specific nucleic acid sequence in the sample is detected without amplification of the specific nucleic acid sequence.

2. The method of claim 1, further comprising:
    introducing a pure buffer solution into one of the hollow-core ARROWs of the planar optofluidic platform, the pure buffer solution being free of nucleic acids; and collecting a signal from the pure buffer solution.

3. The method of claim 2, further comprising:
    comparing the fluorescent signal to the signal from the pure buffer solution.

4. The method of claim 1 further comprising creating a fluorescence correlation spectrum using the fluorescent signal.

5. The method of claim 1, wherein the specific nucleic acid sequence is from a virus.

6. The method of claim 1, wherein the planar optofluidic platform further comprises planar, liquid-core integrated optical waveguides.

7. The method of claim 1, wherein the solid-core ARROWs are connected to different points of the hollow-core ARROWs and the planar optofluidic platform further comprises means for introducing liquid solutions into the hollow-core ARROWs, means for providing an excitation light to the hollow-core ARROWs, and means for collecting a fluorescent signal.

8. The method of claim 1, wherein the solid-core ARROWs are configured to connect to different points of the hollow-core ARROWs, the hollow-core ARROWs and the solid-core ARROWs are configured to provide separate access points for the liquid solution and the light injected into the one of the hollow-core ARROWs and to define optical excitation areas in the sub-picoliter volume.

9. The method of claim 1, wherein the solid-core ARROWs are configured to connect to different points of the hollow-core ARROWs and the planar optofluidic platform further comprises reservoirs at ends of the hollow-core ARROWs configured to at least introduce liquid solutions into the hollow-core ARROWs, a path for an excitation light to enter the hollow-core ARROWs through solid-core ARROWs orthogonally intersecting the hollow-core ARROWs, and a path for collecting a fluorescent signal perpendicularly in the plane of the planar optofluidic platform and for guiding the fluorescent signal to edges of the planar optofluidic platform for detection.

10. The method of claim 1, wherein said introducing the liquid solution is carried out using fluidic reservoirs contained in the planar optofluidic platform.

11. The method of claim 1, wherein said optically exciting the fluorophores is carried out using an excitation light that enters the planar optofluidic platform.

12. The method of claim 1, wherein the planar optofluidic platform is an optofluidic chip and the fluorescent signal is collected perpendicularly in the chip plane of the optofluidic chip and guided to the chip edges of the optofluidic chip for detection.

13. The method of claim 1, further comprising creating a plot of the fluorescent signal.

14. The method of claim 1, wherein said introducing the liquid solution comprises introducing the liquid solution as a stream of the liquid solution and moving the stream of the liquid solution past an optical excitation point contained in the planar optofluidic platform.

15. The method of claim 1, wherein said light is a laser light.

16. The method of claim 1, wherein said converting the fluorescent signal is carried out using a photodiode.

17. The method of claim 1, wherein said converting the fluorescent signal is carried out using an avalanche photodiode.

* * * * *